(12) United States Patent
Kurzweg et al.

(10) Patent No.: US 11,590,012 B2
(45) Date of Patent: Feb. 28, 2023

(54) ORTHOPEDIC DEVICE

(71) Applicant: OTTOBOCK SE & CO. KGAA, Duderstadt (DE)

(72) Inventors: Annedore Kurzweg, Gottingen (DE); Emma Louise Van Den Berg, Enschede (NL); Harry Plechelmus Christenhusz, Bad Bentheim (DE)

(73) Assignee: OTTOBOCK SE & CO. KGAA, Duderstadt (DE)

(*) Notice: Subject to any disclaimer, the term of this patent is extended or adjusted under 35 U.S.C. 154(b) by 269 days.

(21) Appl. No.: 16/085,335

(22) PCT Filed: Mar. 13, 2017

(86) PCT No.: PCT/EP2017/055861
§ 371 (c)(1),
(2) Date: Sep. 14, 2018

(87) PCT Pub. No.: WO2017/157862
PCT Pub. Date: Sep. 21, 2017

(65) Prior Publication Data
US 2019/0083289 A1 Mar. 21, 2019

(30) Foreign Application Priority Data
Mar. 16, 2016 (DE) .......................... 102016104877.1

(51) Int. Cl.
*A61F 5/01* (2006.01)
*A61F 5/058* (2006.01)

(52) U.S. Cl.
CPC ........ *A61F 5/0102* (2013.01); *A61F 5/05841* (2013.01); *A61F 2005/0158* (2013.01); *A61F 2005/0165* (2013.01)

(58) Field of Classification Search
CPC ............... A61F 5/0102; A61F 5/05841; A61F 2005/0158; A61F 2005/0165; A61F 5/01;
(Continued)

(56) References Cited

U.S. PATENT DOCUMENTS 4,576,150 A 3/1986 Auracher
5,146,932 A * 9/1992 McCabe ................... A61F 5/30
602/23
(Continued)

FOREIGN PATENT DOCUMENTS

DE 202011107040 U1 * 12/2011 ............ A61F 5/0113
DE 202011107040 U1 12/2011
(Continued)

OTHER PUBLICATIONS

DE202011107040U1 Machine Translation (Year: 2011).*
(Continued)

*Primary Examiner* — Caitlin A Carreiro
(74) *Attorney, Agent, or Firm* — Holland & Hart LLP

(57) ABSTRACT

An orthopaedic device with a shell mechanism which can be brought into a closed position in which it engages at least partially around a body part arranged in the shell mechanism, and into an open position, in which the body part can be brought into the shell mechanism, wherein the shell mechanism can be brought from the open position to the closed position by means of the body part being introduced into the shell mechanism. The device has at least one actuation element which is arranged and designed in such a way that it is actuated when the body part is introduced into the shell mechanism, and it brings the shell mechanism from the open position to the closed position, wherein the actuation element has a tensile force transmission element, in particular a band or a cloth.

19 Claims, 6 Drawing Sheets

(58) Field of Classification Search
CPC ...... A61F 5/05; A61F 5/0585; A61F 5/05858;
A61F 5/0118; A61F 5/013; A61F 5/02;
A61F 5/37; A61N 2005/1097; A61G
13/123; A41D 13/08
USPC .... 602/5, 12, 15, 16, 19, 20, 23, 26, 27, 60,
602/61–65; 128/846, 869, 877, 878, 882;
2/16
See application file for complete search history.

(56) References Cited

U.S. PATENT DOCUMENTS

| 7,513,881 B1 * | 4/2009 | Grim ..................... A61F 5/0585 |
| | | 602/5 |
| 2007/0131323 A1 * | 6/2007 | Stewart-Stand ....... A45C 13/00 |
| | | 150/131 |
| 2010/0192288 A1 | 8/2010 | Schaaper et al. |
| 2012/0150086 A1 | 6/2012 | Cohen |
| 2014/0257156 A1 * | 9/2014 | Capra .................. A43C 11/165 |
| | | 602/5 |

FOREIGN PATENT DOCUMENTS

| DE | 202011107040 U1 * | 3/2012 | ............ A61F 5/0113 |
| DE | 102013019079 A1 | 5/2015 | |
| EP | 0121718 A1 | 10/1984 | |
| EP | 1452154 A2 | 9/2004 | |
| WO | 2009134858 A1 | 11/2009 | |

OTHER PUBLICATIONS

Machine translation of DE202011107040U1 (Year: 2012).*
PCT International Search Report for PCT International Patent Application No. PCT/EP2017/055861 dated May 30, 2017.

* cited by examiner

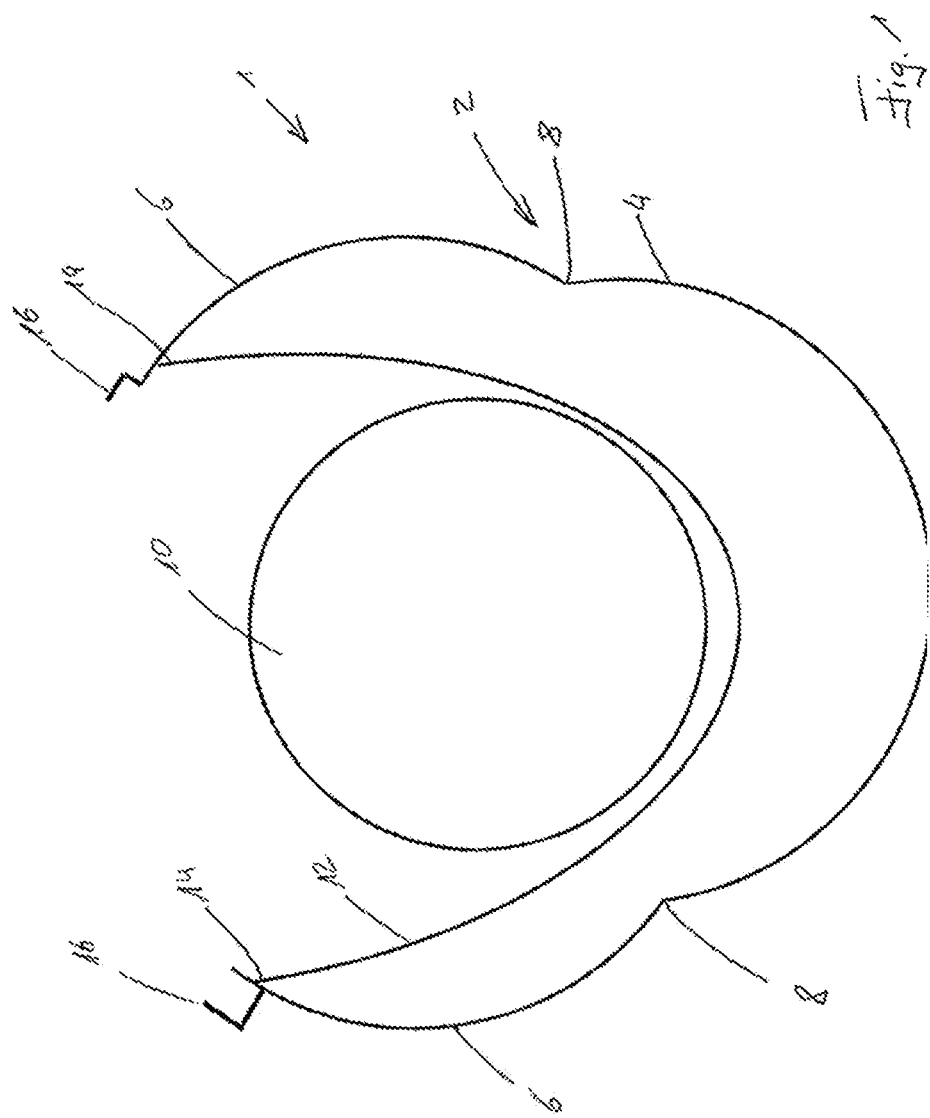

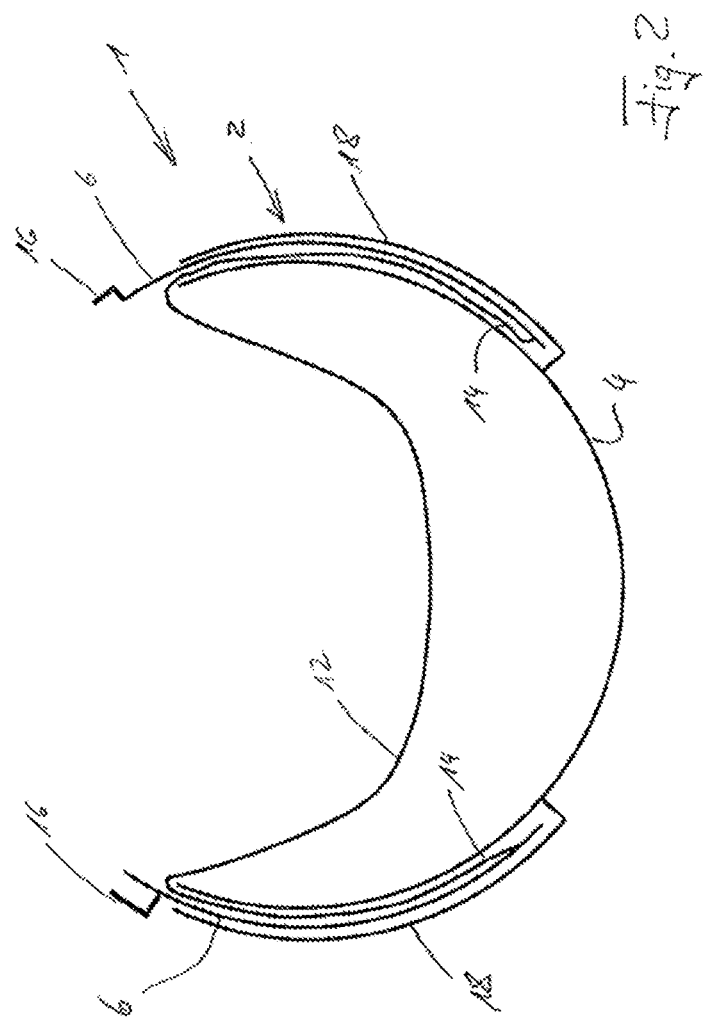

ORTHOPEDIC DEVICE

TECHNICAL FIELD

The invention relates to an orthopaedic device with a shell mechanism which can be brought into a closed position in which it engages at least partially around a body part arranged in the shell mechanism, and into an open position, in which the body part can be brought into the shell mechanism, wherein the shell mechanism can be brought from the open position to the closed position by means of the body part being introduced into the shell mechanism.

BACKGROUND

This type of orthopaedic device may be an orthosis, for example, which is intended for various body parts. This type of orthosis and other orthopaedic devices have a shell mechanism, which at least partially enclose a body part on which the orthosis is to be carried. For instance, ankle foot orthoses or ankle orthoses with a shell mechanism are known that enclose the lower leg of the carrier of the orthosis. Traditionally, belts may be used for this purpose, these belts being arranged around the respective body part and subsequently closed. This may be achieved, for example, by way of velcro elements, clasps or push buttons.

The shell mechanism, such as a belt, can therefore be brought into the closed position in which the body part is often completely, or at least partially, enclosed: this generally results in the orthopaedic device being fixed to the body part of the carrier of the device. However, in order to bring the body part into or move it out of the shell mechanism, it is necessary to bring the shell mechanism into the open position. This occurs, for instance, by releasing a velcro fastener, by opening a clasp or by other means known from the prior art.

However, a disadvantage of this is that at least one hand, often both hands, are required to bring the shell mechanism into the closed position or out of the closed position into the open position. Due to the positioning of the shell device, which is often difficult to access, this is particularly difficult for people with limited motor skills, such as stroke patients. This is even more pertinent given the fact that the hand which is not preferred for motor-related tasks, i.e. the left hand for right-handed people, often has to be used to bring the shell mechanism from the open position into the closed position. With lower arm orthoses or wrist orthoses in particular, one of the hands is the body part on which the shell mechanism is to be arranged, meaning that this hand is not available for bringing the shell mechanism into the closed position.

DE 10 2013 019 079 A1 thus describes a locking system for an orthopaedic aid, such as an ankle foot orthosis, that can be operated with one hand. An element of a magnetic lock is located at the end of a belt that is to be wrapped around a body part. The corresponding second element is arranged on a part of the orthosis that is to be connected using the belt. As it is a magnetic lock, an attractive force between the two elements of the lock increases the closer the two elements get to one another. This results in the lock exhibiting a "self-locating effect", which enables the lock to be closed with just one hand.

DE 20 2011 107 040 U1 describes a further locking device which allows for an orthopaedic brace device to be operated with a single hand. The device described comprises a shell mechanism that constitutes two shells, which are connected to one another via a hinge. In this case, the two shells extend like scissors on both sides of the hinge in such a way that, when in the open state, two ends of the respective shell segments protrude inwards into the interior of the shell mechanism. If, for example, an arm is now inserted into the shell mechanism, the two scissor elements are activated, causing the shells to move towards each other.

However, it is disadvantageous that one hand is needed to close the orthosis and the padding options on the inside of the shell mechanism are limited, given the fact that the scissors-like protruding elements must also be moveable relative to one another in the interior of the shell mechanism. This may result in some uncomfortable situations. Furthermore, the scissors-like clamping also means that the two shell elements can only move relative to one another about a limited swivel angle, and upon opening the orthosis, the body part will be pushed out of the orthosis by the scissors-like protruding projections: this may also cause discomfort to the carrier while wearing the device.

US 2010/0192288 A1 describes padding elements which should protect body parts from exposure to too great a pressure. They comprise a padded layer which clings to the body part that is to be protected when it applies pressure to the padded layer.

SUMMARY

The invention thus aims to further develop an orthopaedic device to ensure an easier hands-free adjustment, including for people with limited motor skills, wherein the disadvantages described above are avoided or at least reduced.

The invention solves the proposed issue by way of an orthopaedic device, characterized in that the device has at least one actuation element which is arranged and designed in such a way that it is actuated when the body part is introduced into the shell mechanism, and it brings the shell mechanism from the open position to the closed position, wherein the actuation element has a tensile force transmission element, in particular a band or a cloth. Consequently, it is not necessary to use one or two hands to bring the shell mechanism into the closed position, for example by having to wrap belts around the body part or close clasp mechanisms. Rather, it is sufficient to insert the body part to which the orthopaedic device is to be arranged into the shell mechanism, which is in the open position. This is the only way to bring the shell mechanism into the closed position such that its arrangement is as easy as possible, even for people with limited motor skills.

The orthopaedic device may be, for instance, an ankle foot orthosis that is worn inside a shoe. It comprises a foot plate, arranged on the base of the foot, and a shell mechanism, which, for example, encompasses the lower leg of the carrier of the orthosis from the front. The ankle foot orthosis can be arranged inside the shoe and put on at the same time as the shoe. If the ankle foot orthosis is an orthopaedic device according to the invention, once the shoe is in place, the carrier of the orthosis need only introduce the lower leg in the designated shell mechanism: this is the only way to bring it in the closed position. If this is the case, the ankle foot orthosis is thus already fully arranged such that complicated handling operations on this part of the human body, which is particularly difficult to reach for people with limited motor skills, are no longer a concern.

According to the invention, the device has at least one actuation element which is arranged and designed in such a way that it is actuated when the body part is introduced into the shell mechanism, and it brings the shell mechanism from the open position to the closed position. The actuation element is actuated upon introduction of the body part into the shell mechanism. In this case, the actuation element can be designed as a sensor or button. For instance, if a sensor identifies that a body part is arranged in the shell mechanism, a control signal is emitted via, for example, an electric control unit. This signal actuates an actuator that, for example, swivels the shell elements, which can be swiveled towards one another, from the first position into the second position. Of course, this can also be done by way of a switch or a button that is activated by the body part when it is inserted into the shell mechanism.

However, it is disadvantageous that this configuration is associated with considerable complexity with regards to its construction, and that a power supply, for instance in the form of a rechargeable battery or a battery, is required.

According to the invention, the actuation element comprises a tensile force transmission element. The use of a band or a cloth has proven itself to be particularly advantageous. This tensile force transmission element is preferably arranged on one or several of the shell elements. In particular, it extends through the shell mechanism in such a way that the body part that is inserted or introduced into the shell mechanism comes into contact with the tensile force transmission element and moves it. This causes a tensile force to be exerted on the moveable shell elements or the shell element capable of elastic deformation, the tensile force causing the respective shell element to be brought from the first position, in which the shell mechanism is in the open position, to the second position. As a result, the shell mechanism is closed and the body part at least partially encompassed.

The tensile force transmission element is preferably connected to the shell mechanism at several points in the circumferential direction of the shell mechanism. This is preferably achieved via rigid spacers, each of which connects one position of the shell mechanism with one position of the tensile force transmission element. In this case, the at least one shell element of the shell mechanism is designed to be elastic, such that a deformation of the at least one shell element occurs by way of the spacers, which are designed to be rigid. This deformation results in an optimal or at least almost optimal adjustment of the shell device and thus of the orthopaedic device to the respective body part of the carrier of the device.

The shell mechanism preferably has at least two shell elements, which can be moved relative to one another and are arranged relative to one another in a first position when the shell mechanism is in the open position, and which are arranged relative to one another in a second position when the shell mechanism is in the closed position. By moving the at last two shell elements relative to one another, the shell mechanism is brought from the open position into the closed position.

The shell elements can preferably be swiveled or moved relative to one another. To this end, hinges may be provided, for example in the form of an integral hinge or as a separate hinge element, these hinges allowing for a swiveling of the shell elements relative to one another.

In a configuration of the shell mechanism that is particularly simple in terms of construction, this is comprised of only two shell elements that are connected to one another such that they can be swiveled. In this case, a bistable hinge joint can be used. Bistable objects are characterized by two stable states into which they can be transformed, for instance, by applying mechanical energy or a force. For example, a bistable hinge can be pre-tensioned in the open position of the two shell elements fixed to it, such that it does not close without the influence of an external force. However, if a force is applied to the hinge by a body part which is introduced into the shell mechanism via the tensile force transmission element, it is transformed into the other stable stable and, for example, clicks into the closed position. A bistable laminar element, such as a band or sheet-shaped element, can be used instead of a hinge, this element also being pre-tensioned and thus comprising two stable positions. Similar devices are known, for example, as reflective strips, which may be provided in a stretched state: they have a curvature that runs parallel to the longitudinal axis and can be transformed into a wound-up state when a force is exerted on the element. This type of bistable laminar element, in particular made of metal and if necessary covered with a plastic, may be used for the shell mechanism.

An effective length of at least one shell element can preferably be adjusted in the circumferential direction of the shell mechanism. As a result, the circumference of the shell mechanism when in the closed position can be changed and adjusted to accommodate the needs and wishes of the carrier of the orthopaedic device. This may occur in various ways. For example, it is conceivable to design the at least one shell element, whose effective length should be changeable, to be made up of several, preferably two, components that can be moved relative to one another in such a way that the effective length can be adjusted by way of a movement of the two components relative to one another. To this end, it is advantageous for one of the components to have at least one slot inside of which a projection of the other component can slide along. In this case, the two components can be fixed relative to one another, for example by means of a screw or clamp connection, preferably in such a way that the fixing is infinitely variable. This renders it possible to individually adjust the length of the shell element according to the carrier's wishes in a simple and quick manner. Alternatively or additionally, a locking device, which the orthopaedic device has in an advantageous configuration, may be arranged on the respective shell element with at least one of its elements. By shifting the position of this at least one element of the locking device, the effective length of the shell element can also be changed.

Additionally or alternatively, the shell mechanism preferably has at least one elastic shell element, which experiences elastic deformation when the shell mechanism is brought from the open position in the closed position or vice-versa. Consequently, this elastic shell element can also be brought into a first position and a second position, the shell mechanism being in the open position when the elastic element is in the first position. If the elastic element is deformed and thus brought in the second position, the shell mechanism is closed and is then in the closed position.

The mechanism preferably comprises at least one locking device, which automatically keeps the shell mechanism in the closed position. In a preferred configuration, this refers to a magnetic lock that is automatically closed when the shell mechanism is brought in the closed position. In order to bring the shell mechanism into the closed position, at least two zones or components of the shell mechanism must be moved towards each other. This may be two zones of a shell element that is capable of elastic deformation or, for example, two shell elements that are designed such that they can be moved relative to one another and, where appropriate, relative to the rest of the orthopaedic device. In this case, a magnetic lock may consist of two permanent magnets or one permanent magnet and a magnetisable element that are arranged in such a way that an attractive force is exerted between both elements of the magnetic lock when the shell mechanism is in the closed position.

For instance, if a tensile force is applied by the tensile force transmission element, for example a band, to two shell elements that can be swiveled, they are brought from the first position into the second position when the body part is inserted into the shell mechanism, thereby bringing the shell mechanism from the open position into the closed position. As a result, the two components of the magnetic lock moved closer together, meaning that the attractive interaction, i.e. the attractive force between both elements, increases. In a preferred configuration, the individual elements of the magnetic lock are arranged in such a way that they support and, where appropriate, finish the closing process, which was started by the tensile force transmission element, such that the two elements of the magnetic lock continue to move towards each other due to the attractive force acting between them. This preferably occurs up until the point they make contact.

In this case, the two components of the locking device, in particular of the magnetic lock, are preferably arranged on different shell elements or on different ends of the same shell element so the closing of the locking device also causes the shell arrangement to transform into the closed state. The effective length of the shell element can be influenced by a change, for instance a shift, in the position of at least one of the components of the locking device on the respective shell element to which it is arranged. In particular, this adjusts the extent to which the two shell elements or the ends of the same shell element overlap when the shell mechanism is in the closed state. A shift or displacement of the individual components of the locking device may occur in numerous ways, for example via a shifting mechanism, velcro elements or via other means.

The orthopaedic device preferably refers to an orthosis, in particular an arm orthosis or a foot or leg orthosis. These can be preferably used for a lower arm, an ankle or a foot. Of course, other orthopaedic devices are possible.

The tensile force transmission element, which can be designed in particular as a laminar element such as a cloth, preferably has reinforcement and/or stiffening elements that ensure a stiffening of the tensile force transmission element along the direction of extension of the shell mechanism. This refers to the direction in which the body part, which is inserted into the shell mechanism, also extends.

It has been proven to be an advantage if the tensile force transmission element has a length that is smaller than the inner circumference of the shell mechanism, the length preferably being adjustable. The insertion or introduction of the body part into the shell mechanism ensures that a force is exerted on the tensile force transmission element.

In a preferred configuration, the orthopaedic device has at least one locking device that automatically keeps the shell mechanism in the closed position, wherein the orthopaedic device preferably does not have further locking devices which do not automatically keep the shell mechanism in the closed position. For example, this type of locking device may be provided in the form of belts, clasps or velcro elements and must be closed by hand. Therefore, within the scope of the present invention, they cannot be deemed to be locking devices that automatically keep the shell mechanism in the closed position.

Even if this type of locking element enabled a further reinforcement of a lock, it would still have the disadvantage that the orthopaedic device could no longer be put in place without using one's hands. Therefore, if the orthopaedic device has only one or several locking devices that automatically keep the shell mechanism in the closed position, the placement of the orthopaedic device is conceivably simple, as only the respective body part has to be introduced into the shell mechanism. This is the only way to close the shell mechanism and arrange the orthopaedic device on the body part.

An orthopaedic device in the sense of the present invention need not necessarily have a medical indication or a corresponding effect. An orthopaedic device in the sense of the present invention should also be understood especially to mean supporting devices that only increase the level of comfort experienced by the carrier of the device. For example, for people who have to perform work tasks above their heads, it is helpful to have an orthopaedic device which is intended to compensate or at least reduce the—in the long term very tiring—impact of gravity on the raised arms. This type of work, which may occur, for example, in the manufacturing industry, but also with professional painting tasks or other work that is performed above one's head, benefits greatly from this type of orthopaedic device and from the possibility of being able to arrange it as quickly and easily as possible. A complicated arrangement by means of several locking devices, belts or bands reduces the acceptance of the orthopaedic device and results in it being used very little or, in the worst case, not at all.

BRIEF DESCRIPTION OF THE DRAWINGS

In the following, an example of an embodiment of the present invention will be explained in more detail by way of the attached drawings: They show:

FIG. 1—a schematic sectional view through an orthopaedic device according to a first example of an embodiment of the invention, FIG. 2—through a device according to a second example of an embodiment of the present invention, FIGS. 3a to 3c—different stages in the arrangement of an orthopaedic device and FIGS. 4a and 4b—different stages in the arrangement of an orthopaedic device according to another example of an embodiment of the present invention.

DETAILED DESCRIPTION

Figure 3A:
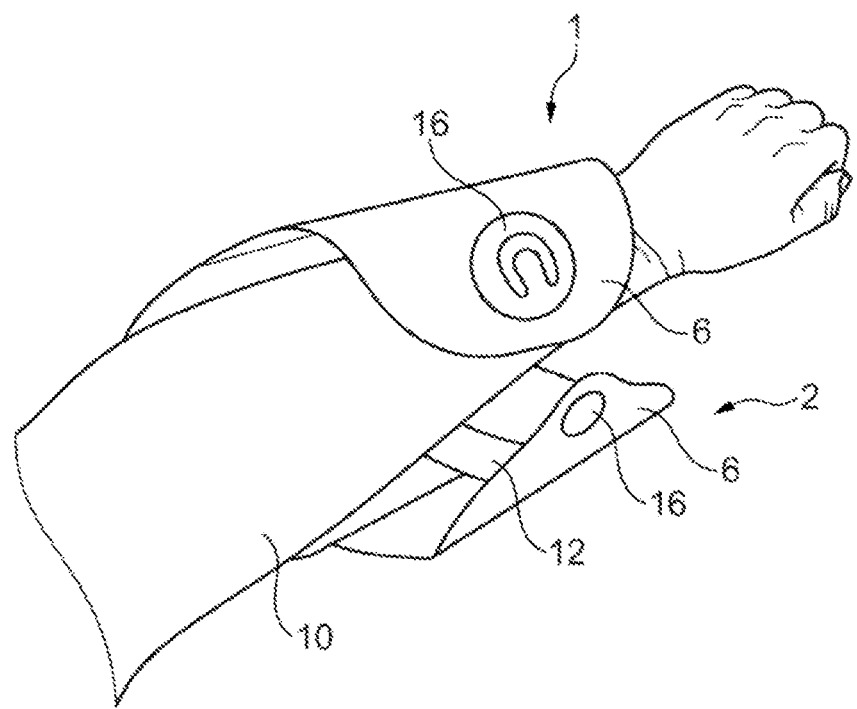

FIG. 1 depicts a schematic sectional view through an orthopaedic device 1 according to a first example of an embodiment of the invention. It comprises a shell mechanism 2, which has a main shell element 4 and two shell elements 6 that can be swiveled relative to the main shell element. The shell elements 6 are mounted on the main shell element 4 by way of hinges 8 such that they (the shell elements) can be pivoted.

FIG. 1 depicts the orthopaedic device 1 with the shell mechanism 2 in the open position. An arm 10, which represents a body part that can be arranged inside the shell mechanism 2, can be introduced from above through the opening between the two shell elements 6. To this end, it is being moved downwards in FIG. 1, thereby coming into contact with an actuation element 12, whose end zones 14 are attached to the shell elements 6. If the arm 10 in FIG. 1 is now moved further downwards, a force aimed in this direction is exerted on the actuation element 12, this force ensuring that the two shell elements 6 swivel around about the hinges 8.

Two locking elements 16 are located at the ends of the shell elements 6, these locking elements being designed, for instance, as magnetic elements of a magnetic locking device.

The force transferred to the shell elements 6 by the arm 10 via the actuation element 12 causes the two locking elements 16 to move towards each other until they come into contact with one another, thereby closing the shell mechanism 2 and preventing an inadvertent opening.

FIG. 2 depicts a second example of an embodiment of the orthopaedic device 1. The main shell element 4 has two pockets 18, one shell element 6 being arranged in each. As is the case in the example of an embodiment depicted in FIG. 1, these are not connected to the main shell element 4 via hinges 8, but are rather arranged inside the pockets 18 such that they can be moved. As in FIG. 1, the actuation element 12 extends through the shell mechanism 2 in such a way that a body part, which is not depicted in FIG. 2, exerts a force on the actuation element 12 when it is introduced into the shell mechanism 2. As the end zones 14 of the actuation element 12 are arranged inside the pockets 18 on the shell elements 6, this type of force and a shifting of the actuation element 12 downwards in FIG. 2 causes the shell elements 6 to move out of the pockets 18. The locking elements 16 are also visible at the ends of the shell elements 6, the locking elements being part of a locking device.

Figure 3B:
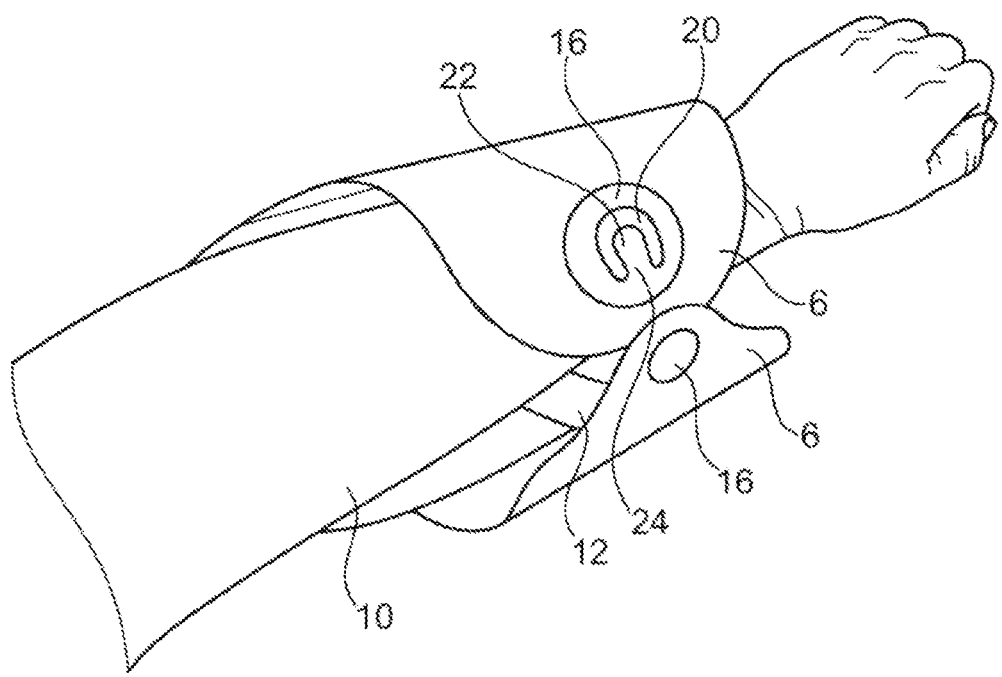
Figure 3C:
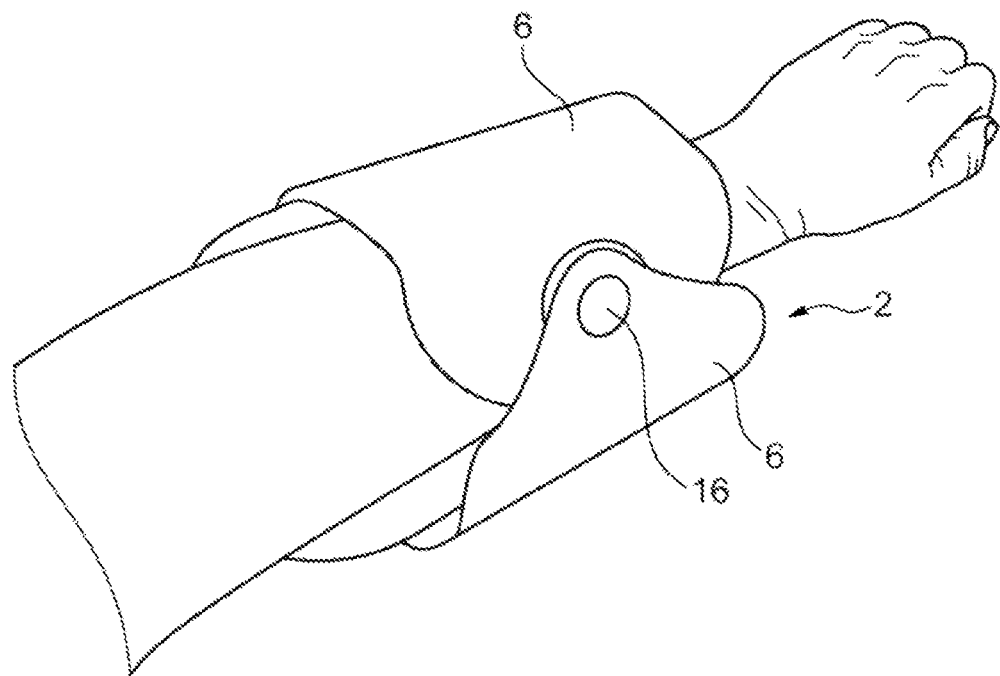

FIGS. 3a to 3c show different stages in the arrangement of the orthopaedic device 1. In the example of an embodiment depicted, the shell mechanism 2 is intended to accommodate the arm 10. It has two shell elements 6 between which an actuation element 12 is arranged. In FIG. 3a, the shell mechanism 2 is depicted in the open position: the arm 10 has just been introduced. Locking elements 16 can be recognised on the two shell elements 6: in the example of embodiment depicted, the locking elements are a magnetic lock. By inserting the arm 10 into the shell mechanism 2, the actuation element 12 is actuated and, in this case, a force is exerted on the two shell elements 6 which ensures that the two locking elements 16 are moved towards one another.

This is shown in FIG. 3b. The two locking elements 16 have clearly been moved towards one another by activating the actuation element 12. Due to the fact that the two locking elements 16 are designed to be magnetic in the example of the embodiment depicted, an attractive force is present between them which ensures that a further movement of the two locking elements 16 towards one another takes place. At the top of the locking element 16 depicted in FIG. 3b, it should be recognised that it comprises an open ring 20 on one side, which is designed as a protrusion and therefore has a recess 22 in its centre. It has an opening 24, at the bottom in FIG. 3b, through which the locking element 16 depicted at the bottom in FIG. 3b can be introduced. The advantage of this is that, if the ring 20, the recess 22 and the lower locking element 16 are cleverly designed, a positive locking occurs alongside the magnetic holding force. To open the locking device, the two locking elements 16 must be moved towards each other in precisely the opposite direction. If this does not happen and a force is applied in another direction, in addition to the magnetic holding force, the positive locking also takes effect.

This is shown in FIG. 3c. The shell mechanism 2 can be recognised in the closed position, which is further secured by the two locking elements 16.

Figure 4A:
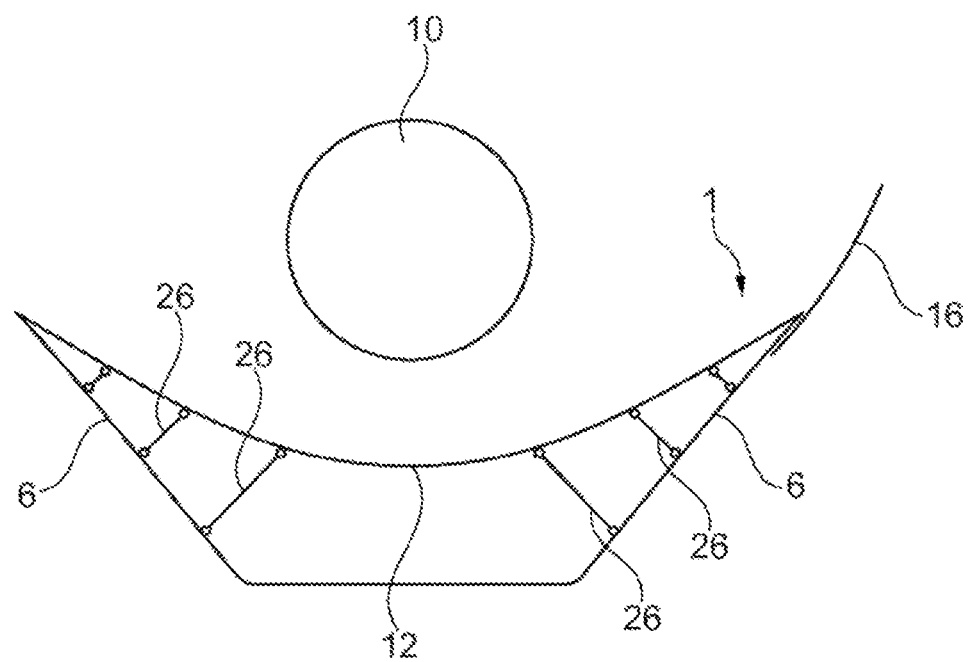
Figure 4B:
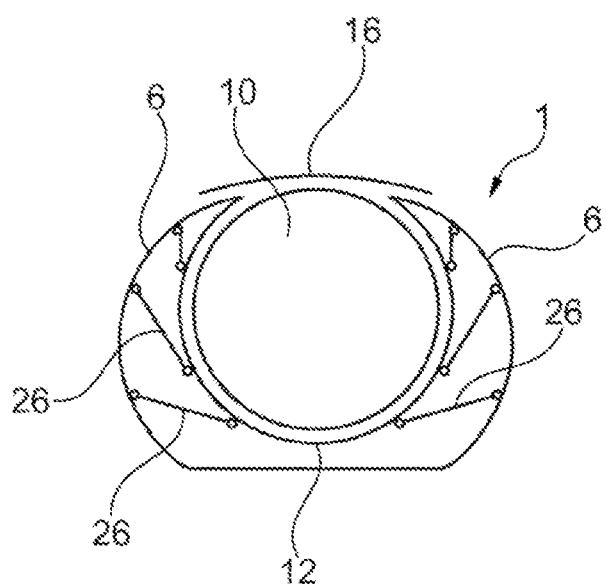

FIGS. 4a and 4b depict a cross section of a further embodiment of the orthopaedic device 1. As is the case with the previous configurations, the actuation element 12 is designed to be a tensile force transmission element. The device has a shell mechanism 2 with two shell elements 6, which are designed to be straight and not curved when in the open position depicted in FIG. 4a. Of course, the shell elements 6 may also have a curvature. Spacers 26 are positioned between the tensile force transmission element 12 and the respective shell elements 6, these spacers preferably being designed to be rigid and maintaining a distance between the two components that they connect. The device also has a locking element 16.

If the arm 10 or another body part, which is to be inserted into the shell mechanism 2, of the carrier of the orthopaedic device 1 is now inserted into the shell mechanism 2, this ensures—in the embodiment depicted in FIGS. 4a and 4b—that the closed position shown in FIG. 4b is reached. The spacers 26 can make use of the so-called Fin Ray Effect, which ensures a special curvature of the elastic shell elements 6. The locking element 16 seals the rest of the opening between the two shell elements 6 The body part, i.e. in this case, the arm 10, is securely enclosed and the orthopaedic device 1 can be arranged without the additional aid of a hand.

The tensile force transmission element may have at least one stiffening element, by means of which a flexibility of the tensile force transmission element along an extension direction of the shell mechanism is reduced. The tensile force transmission element may have a length that is shorter than an inner circumference of the shell mechanism in the closed position, wherein the length is preferably adjustable.

REFERENCE LIST 1 orthopaedic device
3 shell mechanism
4 main shell element
6 shell element
8 hinge
10 arm
12 actuation element
14 end zone
16 locking element
18 pocket
20 ring
22 recess
24 opening
26 spacers

The invention claimed is:

1. An orthopedic device comprising:
a shell mechanism configured to have an open position, configured for a body part to be brought into the shell mechanism, and a closed position, in which the shell mechanism is configured to be engaged at least partially around the body part arranged in the shell mechanism;
at least one actuation element which is configured to be actuated when the body part is introduced into the shell mechanism, and which brings the shell mechanism from the open position to the closed position, wherein the at least one actuation element comprises a tensile force transmission element, the tensile force transmission element having a length that is shorter than an inner circumference of the shell mechanism in the closed position;
wherein the tensile force transmission element extends in the shell mechanism and is configured such that the body part inserted into the shell mechanism contacts and moves the tensile force transmission element thereby applying a tensile force that moves the shell mechanism from the open position to the closed position to partially encompass the body part, and wherein the tensile force transmission element is a cloth.

2. The orthopedic device according to claim 1, wherein the shell mechanism has at least two shell elements, which are configured to be moved relative to one another and be arranged relative to one another in a first position when the shell mechanism is in the open position, and which are arranged in a second position when the shell mechanism is in the closed position.

3. The orthopedic device according to claim 2, wherein the at least two shell elements are configured to be swivelled or moved relative to one another.

4. The orthopedic device according to claim 2, wherein an effective length of at least one of the at least two shell elements is configured to be adjusted in the circumferential direction of the shell mechanism.

5. The orthopedic device according to claim 1, further comprising at least one locking device that is configured to automatically maintain the shell mechanism in the closed position.

6. The orthopedic device according to claim 5, wherein the at least one locking device comprises at least one magnetic lock configured to automatically close when the shell mechanism is brought into the closed position.

7. The orthopedic device according to claim 1, wherein the shell mechanism has at least one elastic shell element which is configured to experience elastic deformation when the shell mechanism is brought from the open position to the closed position or from the closed position to the open position.

8. The orthopedic device according to claim 1, wherein the orthopedic device is an arm orthosis, a foot orthosis, or a leg orthosis.

9. The orthopedic device according to claim 1, wherein the tensile force transmission element has at least one stiffening element configured to reduce a flexibility of the tensile force transmission element along an extension direction of the shell mechanism.

10. The orthopedic device according to claim 1, wherein the length of the tensile force transmission element is adjustable.

11. An orthopedic device comprising:
a shell mechanism operable between an open position configured for a body part to be introduced into the shell mechanism and a closed position in which the shell mechanism is configured to at least partially surround and engage the body part arranged in the shell mechanism;
at least one actuation element configured to be actuated when the body part is introduced into the shell mechanism, the at least one actuation element moving the shell mechanism from the open position to the closed position and comprising a tensile force transmission element, the tensile force transmission element having a length that is shorter than an inner circumference of the shell mechanism in the closed position;
wherein the tensile force transmission element extends in the shell mechanism and is configured such that the body part inserted into the shell mechanism contacts and moves the tensile force transmission element thereby applying a tensile force that moves the shell mechanism from the open position to the closed position to at least partially surround and engage the body part, and wherein the tensile force transmission element is a cloth.

12. The orthopedic device according to claim 11, wherein the shell mechanism has at least two shell elements, which are configured to be moved relative to one another and are arranged relative to one another in a first position when the shell mechanism is in the open position, and which are arranged in a second position, different from the first position, when the shell mechanism is in the closed position.

13. The orthopedic device according to claim 12, wherein the at least two shell elements are movable relative to one another.

14. The orthopedic device according to claim 12, wherein an effective length of at least one of the at least two shell elements is configured to be adjusted in the circumferential direction of the shell mechanism.

15. The orthopedic device according to claim 11, further comprising at least one locking device that is configured to automatically maintain the shell mechanism in the closed position.

16. The orthopedic device according to claim 15, wherein the at least one locking device comprises at least one magnetic lock configured to automatically close when the shell mechanism is brought into the closed position.

17. The orthopedic device according to claim 11, wherein the shell mechanism has at least one elastic shell element which is configured to elastically deforms deform when the shell mechanism is brought from the open position to the closed position or from the closed position to the open position.

18. The orthopedic device according to claim 11, wherein the orthopedic device is an arm orthosis, a foot orthosis or a leg orthosis.

19. The orthopedic device according to claim 11, wherein the tensile force transmission element has at least one stiffening element configured to reduce a flexibility of the tensile force transmission element along an extension direction of the shell mechanism.

* * * * *